United States Patent
Fein et al.

(10) Patent No.: US 6,571,113 B1
(45) Date of Patent: May 27, 2003

(54) OXIMETER SENSOR ADAPTER WITH CODING ELEMENT

(75) Inventors: Michael E. Fein, Mountain View, CA (US); Bradford B. Chew, San Ramon, CA (US)

(73) Assignee: Mallinckrodt, Inc., Hazelwood, MO (US)

( * ) Notice: Subject to any disclaimer, the term of this patent is extended or adjusted under 35 U.S.C. 154(b) by 11 days.

(21) Appl. No.: 09/668,127

(22) Filed: Sep. 21, 2000

(51) Int. Cl.[7] .................................................. A61B 5/00
(52) U.S. Cl. ........................ 600/323; 600/322; 600/310
(58) Field of Search ................ 600/310–311, 322–324, 600/331; 385/20; 439/488–489, 620–622

(56) References Cited

U.S. PATENT DOCUMENTS

| | | | | |
|---|---|---|---|---|
| 5,807,247 A | * | 9/1998 | Merchant et al. ........... | 600/310 |
| 5,818,985 A | * | 10/1998 | Merchant et al. ............. | 385/20 |
| 5,987,343 A | * | 11/1999 | Kinast ........................ | 600/323 |
| 5,995,855 A | * | 11/1999 | Kiani et al. .................. | 600/310 |
| 5,997,343 A | * | 12/1999 | Mills et al. .................. | 439/489 |

* cited by examiner

*Primary Examiner*—Eric F. Winakur
*Assistant Examiner*—Matthew Kremer
(74) *Attorney, Agent, or Firm*—Townsend and Townsend and Crew LLP

(57) ABSTRACT

An oximeter sensor adapter which allows a sensor without a resistor in parallel with its LEDs to operate with an oximeter expecting such a resistor in parallel. The adapter includes LED drive electronics and appropriate oximeter drive current sensing circuitry for converting the drive signals from the oximeter into appropriate LED drive signals for the sensor. Instead of a resistor being on the sensor in parallel with one or more of the LEDs, the resistor is placed across the leads in front of the LED drive electronics and oximeter drive current sensing circuitry, on the oximeter side of the adapter. By providing LED drive electronics and oximeter drive current sensing circuitry which do not draw significant current at a low voltage, the oximeter is able to measure the resistor independently just as if it were in parallel with the LEDs.

14 Claims, 13 Drawing Sheets

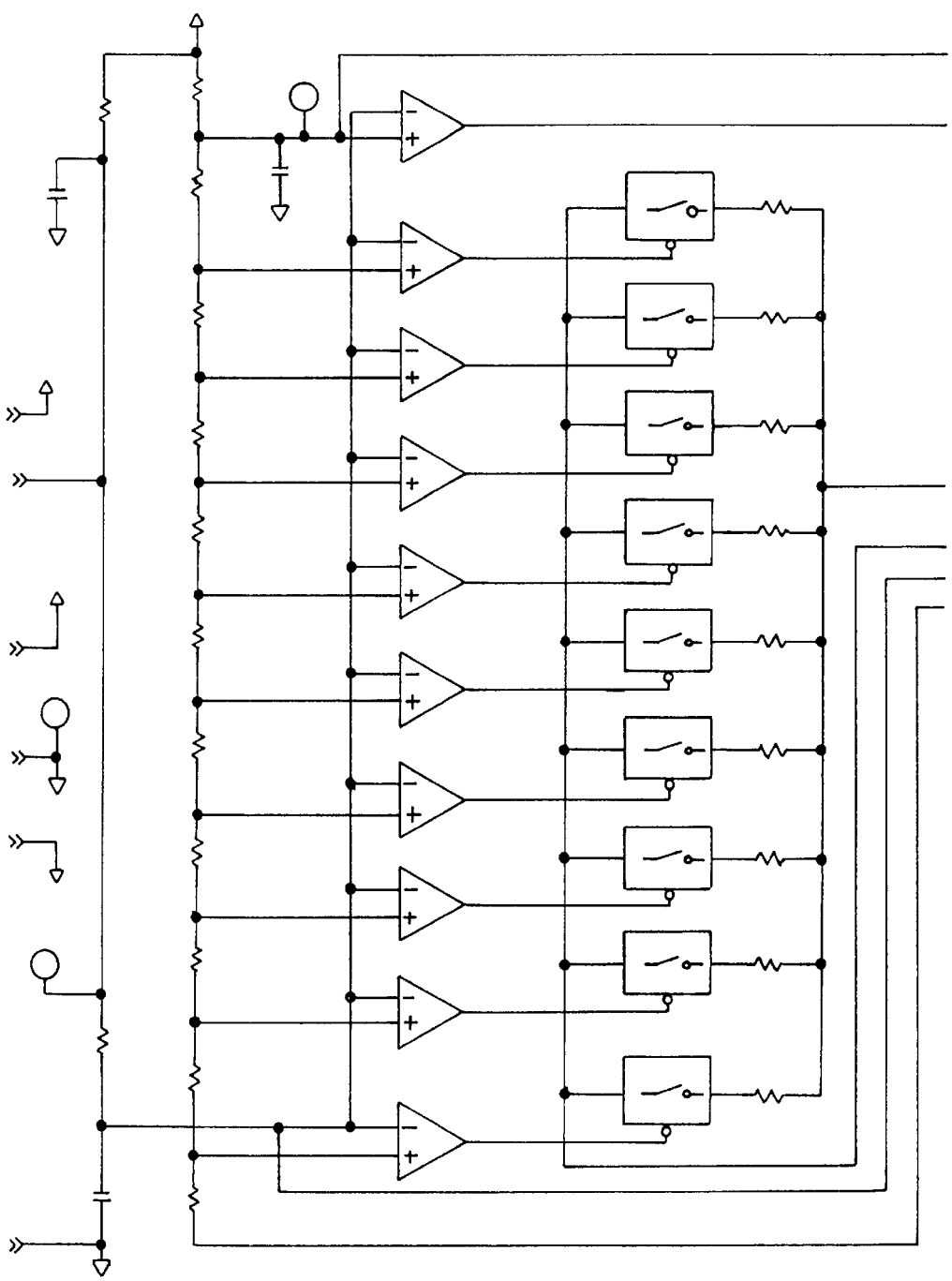
*FIG. 9A.*
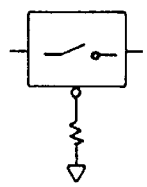

OXIMETER SENSOR ADAPTER WITH CODING ELEMENT

BACKGROUND OF THE INVENTION

This invention relates in general to optical oximeters and relates more particularly to an adapter that enables an optical oximeter probe, that is designed/configured to be utilized on an associated oximeter monitor, to be used on a different oximeter monitor that utilizes a different probe configuration.

Because of the importance of oxygen for healthy human metabolism, it is important to be able to measure the oxygen content of a patient's blood. The monitoring of a patient's arterial hemoglobin oxygen saturation during and after surgery is particularly critical.

Noninvasive oximeters have been developed that direct light through a patient's skin into a region, such as a finger, containing arterial blood. This light typically contains two or more primary wavelengths of light. Examples of such oximeters are disclosed in U.S. Pat. No. 5,209,230 entitled "Adhesive Pulse Oximeter Sensor With Reusable Portion" issued to Swedlow, et al. and in U.S. Pat. No. 4,700,708 entitled "Calibrated Optical Oximeter Probe" issued to New, Jr. et al., both assigned to the assignee of the present invention, the disclosures of which are incorporated herein by reference. The oximeter in the patent by New, Jr. et al. includes a probe that contains a resistor having a resistance that can be measured by a monitor to which the probe is attached. The measured value of this resistance is indicative of the wavelengths of the light directed from the light emitting diodes (LEDs) through the patient's epidermis. The monitor uses this information and the measured intensities of light detected at those wavelengths to calculate the blood arterial oxygen content of the patient. The LEDs are activated in non-overlapping temporal intervals, so that the amount of absorption of light at each of these two wavelengths is measured separately.

Oftentimes, an oximeter sensor may be made by one manufacturer, and a monitor by another manufacturer. Accordingly, adapters may be necessary if the sensor and the oximeter are not compatible. Alternately, the sensor itself can be configured so that it can be used with different oximeters. For example, U.S. Pat. No. 5,249,576, entitled "Universal Pulse Oximeter Probe" issued to Goldberger et al., allows the leads of the sensor to be connected in alternate configurations. Examples of adapters are set forth For a further understanding of the nature and advantages of the invention, reference should be made to the following description taken in conjunction with the accompanying drawings.

DESCRIPTION OF THE SPECIFIC EMBODIMENTS

Figure 1:
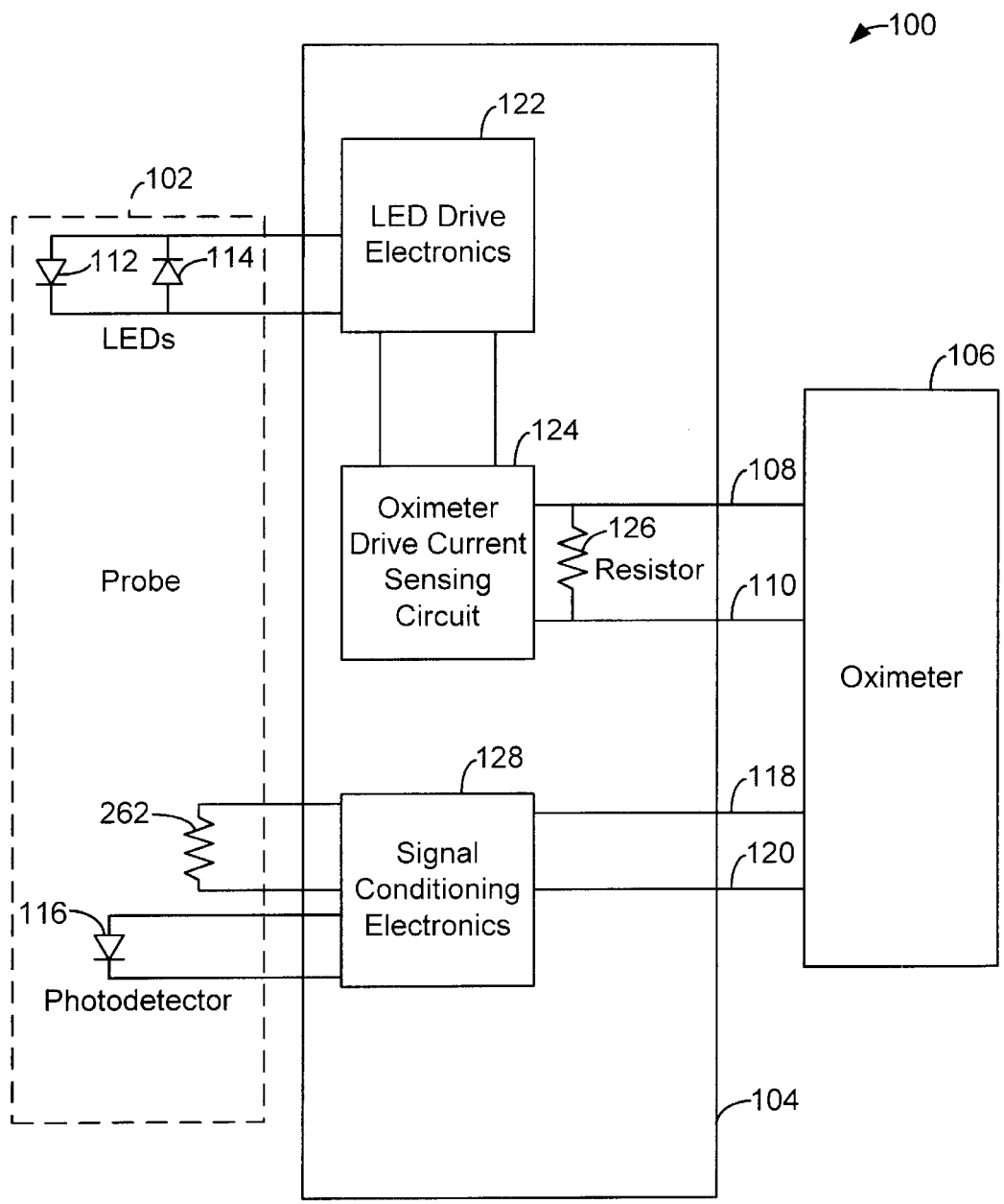
FIG. 1 is a block diagram of an oximeter system including an adapter according to the present invention.

FIG. 1 shows an oximeter system 100 with a pulse oximeter probe 102, an adapter 104, and an oximeter 106. Oximeter 106 provides LED drive signals on lines 108 and 110, which it expects to be coupled to the input lines to LEDs 112 and 114 of sensor 102. A photodetector 116 from the sensor provides photodetector signals which are eventually provided on photodetector input lines 118 and 120 of oximeter 106.

Adapter 104 includes LED drive electronics 122, which may be controlled by oximeter drive current sensing circuit 124. This circuitry allows the drive signals to be converted from the levels output by oximeter 106 to the desired levels for a particular probe 102. In addition, in one embodiment, a three-level drive signal including a third lead from the oximeter may be converted into a two lead drive signal to probe 102, or vice-versa.

A resistor 126 is placed across the drive lines 108 and 110. This resistor mimics the resistance expected by the oximeter to be in the sensor in parallel with the LEDs. This resistor may be read, for example, by applying a low voltage which normally would not activate the LEDs. As long as oximeter drive current sensing circuit 124 and in U.S. Pat. No. 5,807,247, assignee Nellcor Puritan Bennett, Inc., and in U.S. Pat. No. 5,818,985, also assigned to Nellcor Puritan Bennett, Inc. Yet another adapter is set forth in U.S. Pat. No. 6,023,541, entitled "Active Optical Oximeter Probe Adapter", Adnan Merchant et al., also assigned to Nellcor Puritan Bennett, Inc.

In one type of oximeter sensor, set forth in Masimo Corporation U.S. Pat. No. 5,758,644, separate leads on the sensor for connecting to a coding resistor are eliminated. Instead, the coding resistor is connected in parallel with the light-emitting diodes (LEDs) of the sensor. The coding resistor can be read by providing a low voltage at which the LEDs will not conduct. For example, a voltage of 0.5 volts will accomplish this. Thus, in a configuration mode, a low voltage can be driven to the LED leads, and the resistance can be read. Subsequently, higher voltages can be used for driving the LEDs in an operational configuration. Clearly, oximeter sensors with separate LED leads will not be compatible with such an arrangement.

SUMMARY OF THE INVENTION

The present invention provides an oximeter sensor adapter which allows a sensor without a resistor in parallel with its LEDs to operate with an oximeter expecting such a resistor in parallel. The adapter includes LED drive electronics and appropriate oximeter drive current sensing circuitry for converting the drive signals from the oximeter into appropriate LED drive signals for the sensor. Instead of a resistor being on the sensor in parallel with one or more of the LEDs, the resistor is placed across the leads in front of the LED drive electronics and oximeter drive current sensing circuitry, on the oximeter side of the adapter. By providing LED drive electronics and oximeter drive current sensing circuitry which do not draw significant current at a low voltage, the oximeter is able to measure the resistor independently just as if it were in parallel with the LEDs.

Thus, the present invention in essence fools the oximeter into thinking there is a resistor connected in parallel with the LEDs, when in fact there is not. In one embodiment, the adapter may also include signal conditioning electronics between the photodetector on the sensor and the photodetector input leads to the oximeter. This allows adjusting for a number of factors, such as a coding resistor value which may not correspond to the LED wavelength as expected by the oximeter. LED drive electronics 122 do not draw much current at such a low voltage, the resistor 126 can have its value read.

In addition, the adapter provides, in one embodiment, signal conditioning electronics 128. This can modify the photodetector signal as appropriate. For example, the signal conditioning electronics may modify the photodetector signals to compensate for the LEDs having wavelengths which don't match resistor 126 as expected by oximeter 106. This can be compensated for, along with variations from the expected wavelength of the LEDs, by appropriate modification of the photodetector signal with signal conditioning electronics 128.

Figure 2:
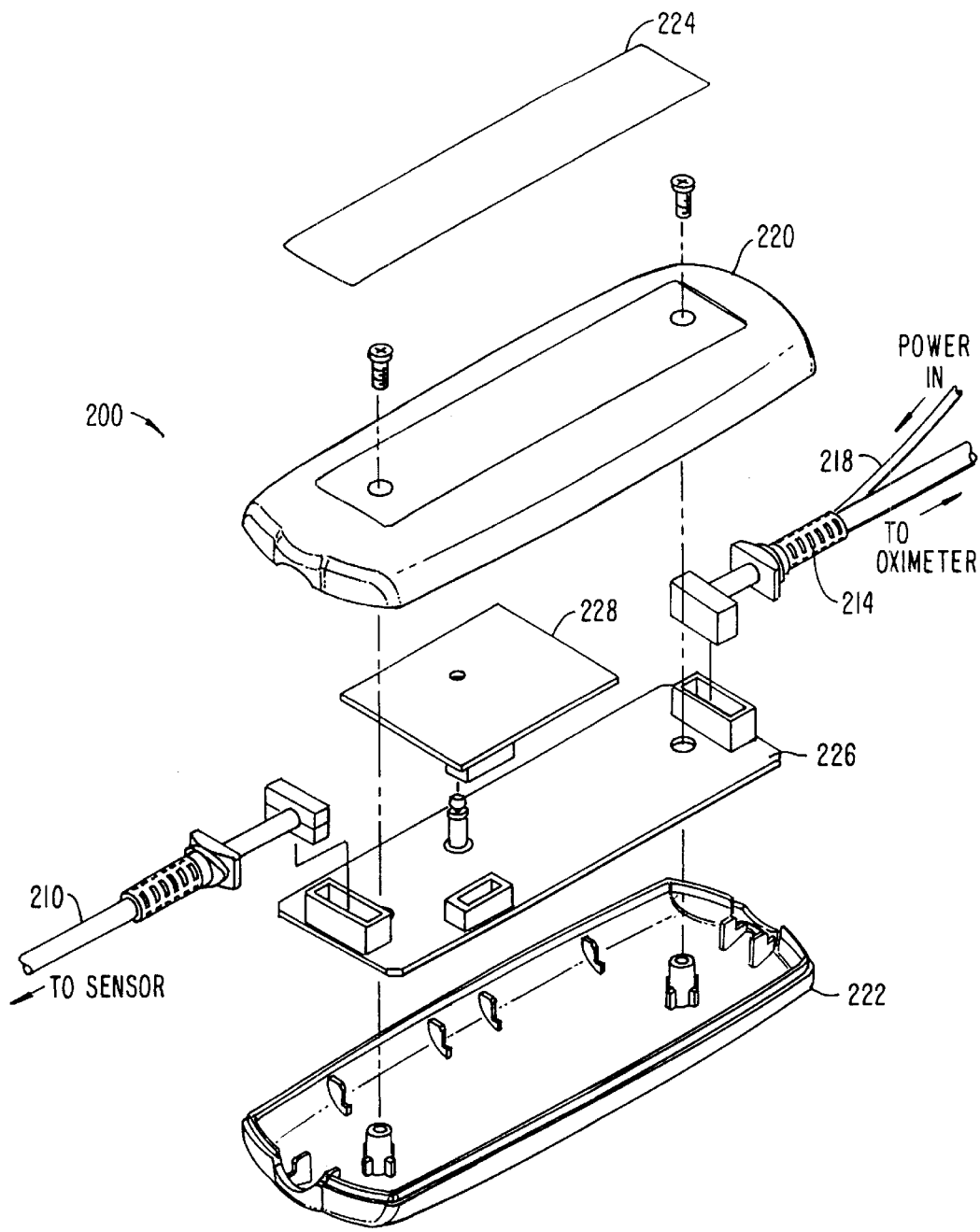
FIG. 2 is an exploded view of an embodiment of a housing for an adapter according to the invention.

FIG. 2 is an exploded view of one embodiment of an adapter or translator 200 according to the invention. The adapter is connected by a cable 210 to a sensor or probe. Another cable 214 attaches to an oximeter monitor. A separate power cable 218 provides power to the electronics of adapter 200.

Shown are an upper housing shell 220 with an associated label 224, and a lower housing shell 222. The cables connect to an internal motherboard 226 which holds electronic components of the adapter. A daughterboard 228 holds circuitry for converting the detector signal to take into account a different LED wavelength from what the oximeter anticipates, as discussed in more detail below. This is sometimes referred to as a ratio of ratios conversion, or RAT/RAT conversion.

Figure 3:
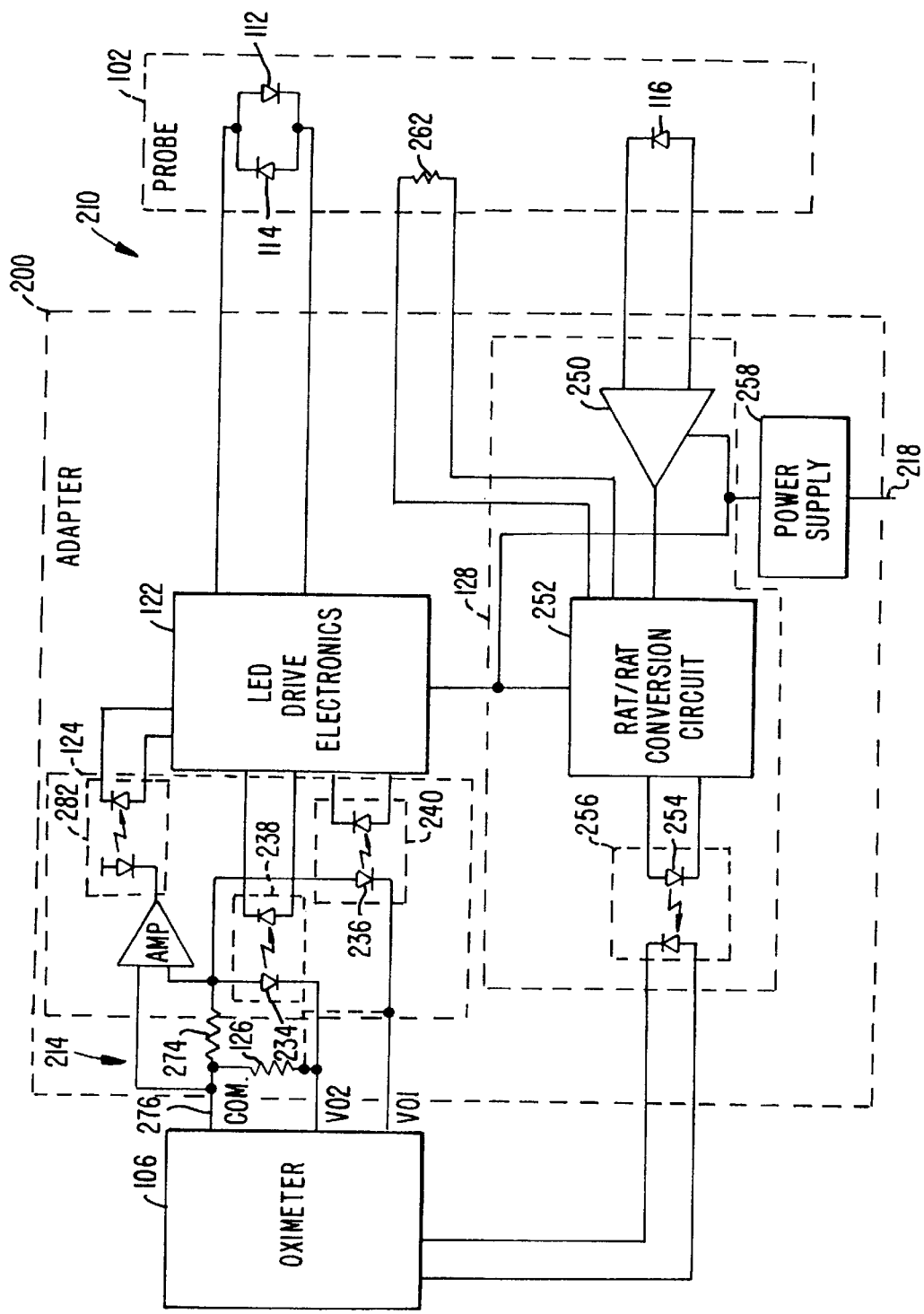
FIG. 3 is a block diagram of an adapter according to a 3-wire embodiment of the present invention.

FIG. 3 is a block diagram of an oximeter, a probe, and electronic circuits contained in adapter 200. An oximeter 106 is shown, with electrical cable 214 consisting of lines VO1, VO2 and COM. The power cable 218 is shown at the bottom of FIG. 3. Also shown is the probe 102, along with the lines making up cable 210.

FIG. 3 shows an embodiment in which the monitor outputs three LED drive lines, VO1, VO2 and COM. These drive lines are for a sensor configuration in which the two LEDs are not mounted in parallel, but rather back-to-back with the third, or common line (COM) in-between. The particular embodiment of FIG. 3 shows a conversion from the three-wire drive lines to a two-wire sensor. However, the present invention could be applied in cases in which the monitor drives only two lines for a two-line sensor as shown in FIG. 4, or alternately, for a two-drive-line monitor and a three-drive-line sensor.

As can be seen in FIG. 3, resistor 126 of FIG. 1 is connected between common line 276 and one or the other of the drive lines VO1 and VO2, as indicated by dashed lines. The following description sets forth the rest of the circuitry, which is also described in U.S. Pat. No. 6,023,541, incorporated herein by reference.

Three LED drive lines, marked COMMON, VO1 and VO2, are shown coming out of oximeter 106. These connect to first and second LEDs 234 and 236. These are connected in the manner expected to be seen in an actual probe by monitor 106. Instead, however, the LEDs are each part of an optical isolator element, elements 238 and 240. The optically sensed signal through LEDs 234 and 236 are thus provided to an LED drive circuit 122. Circuit 122 provides the necessary conversion and drives a pair of LEDs 112 and 114 in probe 102, which are connected in a two-lead, anti-parallel arrangement. Thus, LED drive circuit 122 converts the signals from the three-lead configuration of LEDs 234 and 236 to the two-lead, anti-parallel configuration of LEDs 112 and 114.

Figure 4:
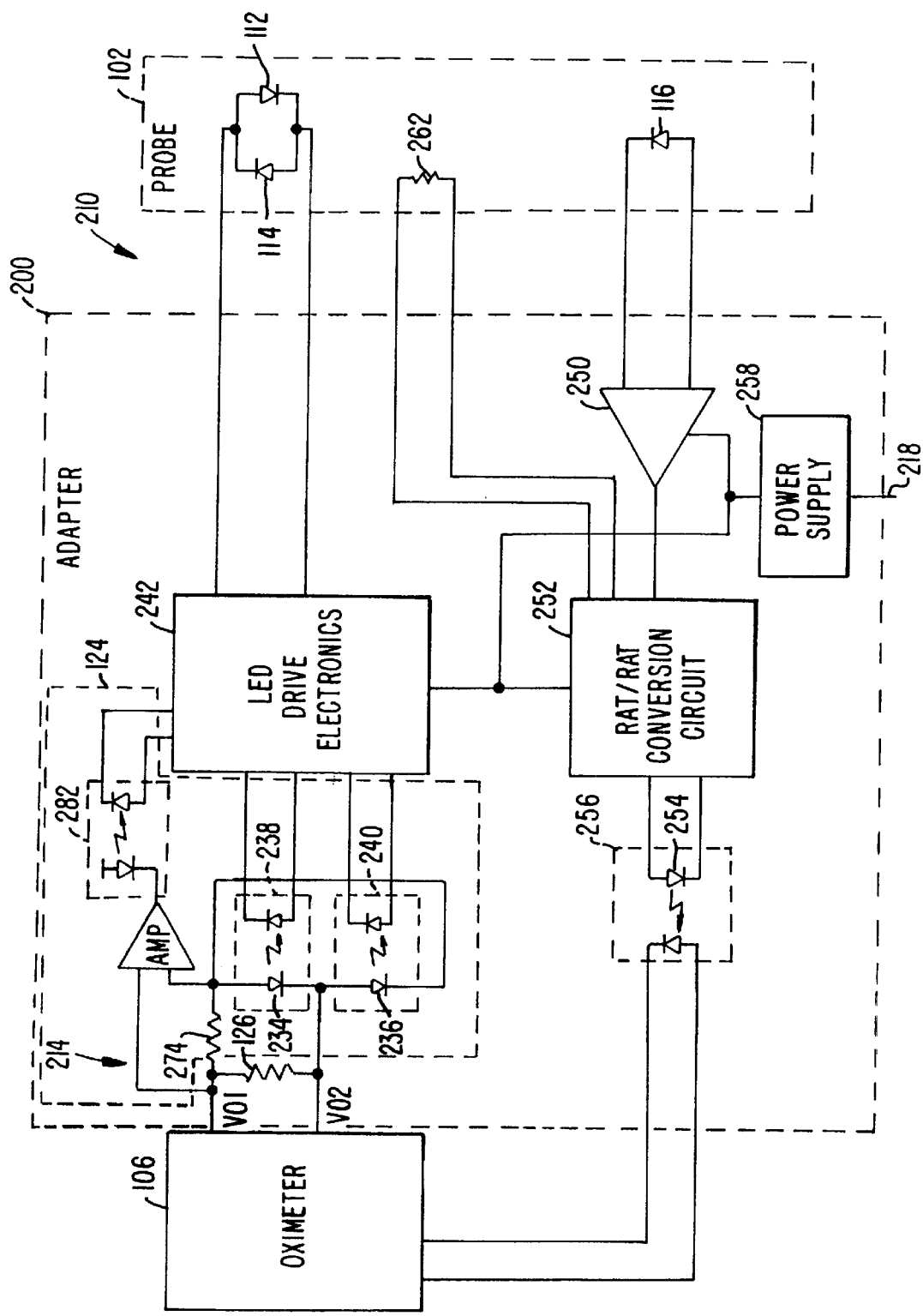
FIG. 4 is a block diagram of an adapter according to a 2-wire embodiment of the present invention.

As can be seen in FIG. 4 (which illustrates a two-drive-line LED embodiment), resistor 126 of FIG. 1 is connected between the two drive lines VO1 and VO2. The following description sets forth the rest of the circuitry.

The two LED drive lines, marked VO1 and VO2, are shown coming out of oximeter 106. These connect to the first and second LEDs 234 and 236. These are connected in the manner expected to be seen in an actual probe by oximeter 106. Instead, however, the LEDs are each part of an optical isolator element, elements 238 and 240. The optically sensed signal through LEDs 234 and 236 are thus provided to an LED drive circuit 122. Circuit 122 provides the necessary conversion and drives a pair of LEDs 112 and 114 in probe 102, which are also connected in a two-lead, anti-parallel arrangement. Thus, LED drive circuit 122 converts the signals from the monitor's two-lead anti-parallel configuration of LEDs 234 and 236 (in parallel with resistor 126) to the probe's two-lead, anti-parallel configuration of LEDs 244 and 246 with a separate coding element such as resistor 262.

In both FIGS. 3 and 4, a transformation is provided for the signals from the photodetector 116 in probe 102. The signals are provided to an amplifier 250, and then to a RAT/RAT conversion circuit 252. The output of the conversion circuit is provided through another LED 254 in an opto-isolator 256, which is then provided to oximeter 106. As can be seen, the circuitry of the adapter is electrically isolated from oximeter 106, and is separately powered by a power supply 258. The electrical isolation provides patient isolation from ground.

RAT/RAT conversion circuit 252 is used because the actual LEDs 112 and 114 of probe 102 may have different wavelengths than expected by oximeter 106. This will result in incorrect calculation of oxygen saturation by oximeter 106. To compensate for this, the actual value of the detected signal is modified accordingly, thus compensating for the fact that different coefficients are used than should be for the actual LEDs. This is done by conversion circuit 252, in a manner described in more detail in U.S. Pat. No. 5,807,247, assigned to Nellcor Puritan Bennett, Inc.

Figure 5:
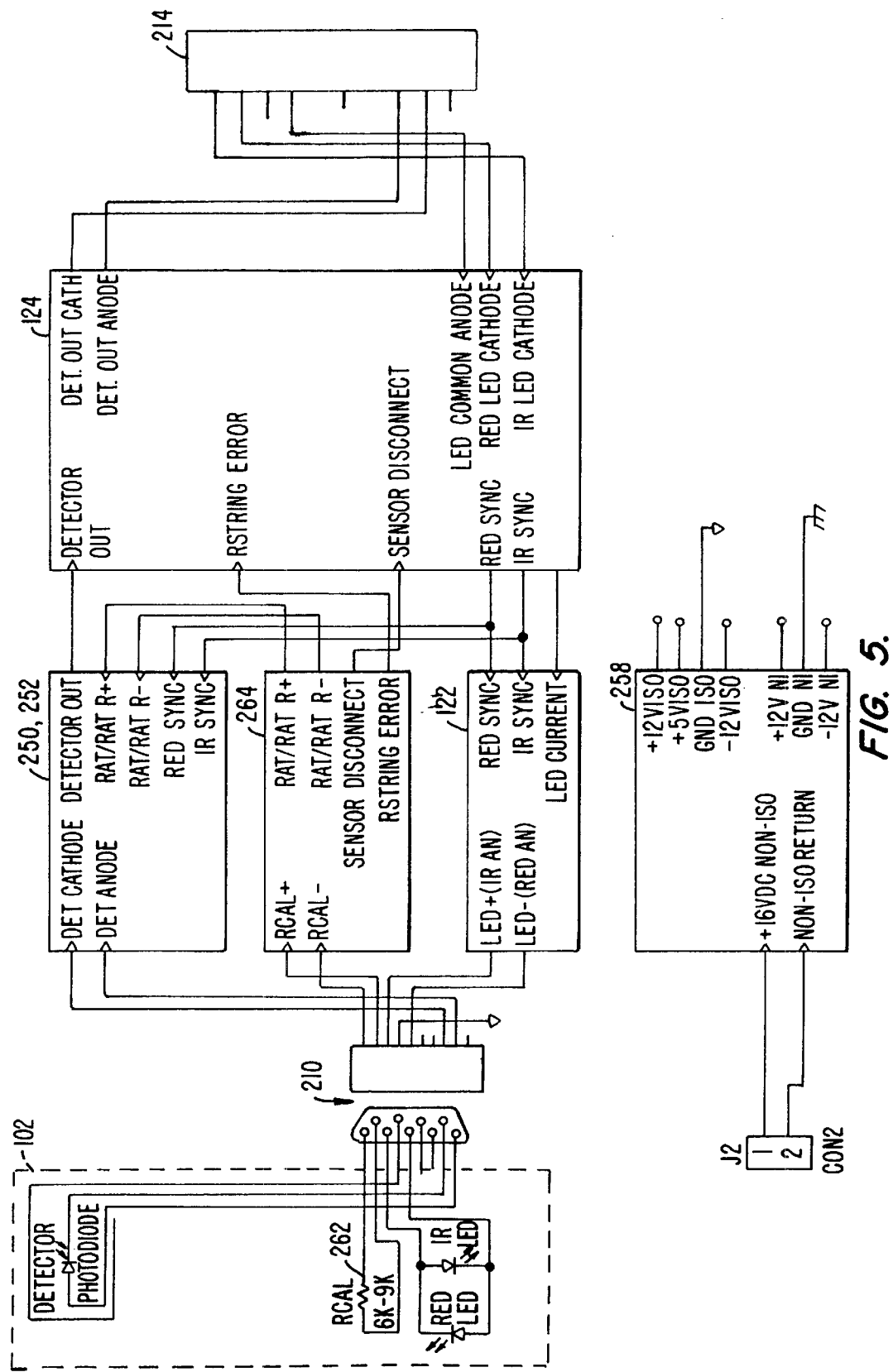
FIG. 5 is a block diagram illustrating some of the elements of FIG. 3.

FIG. 5 is another block diagram illustrating other aspects of the embodiment of FIG. 3. The multiple optical isolators are shown generally as isolation interface 260. Additionally, a calibration resistor 262 is shown in probe 102. A decoder circuit 264 is provided to select the appropriate gains in the RAT/RAT circuit.

Figure 6A:
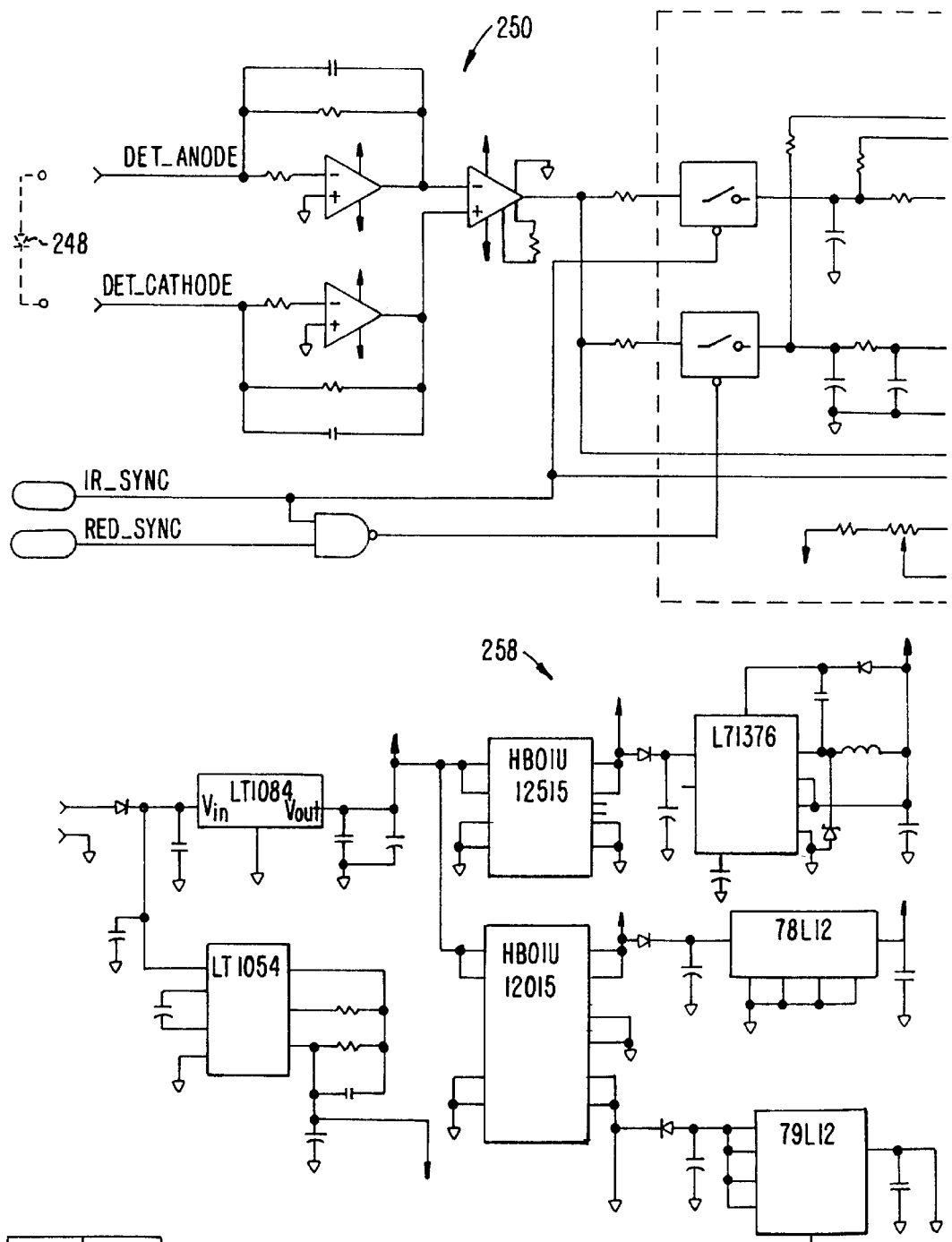
FIGS. 6–9 are circuit diagrams illustrating one embodiment of the circuits of FIG. 5 for 2-wire and 3-wire embodiments.
Figure 6B:
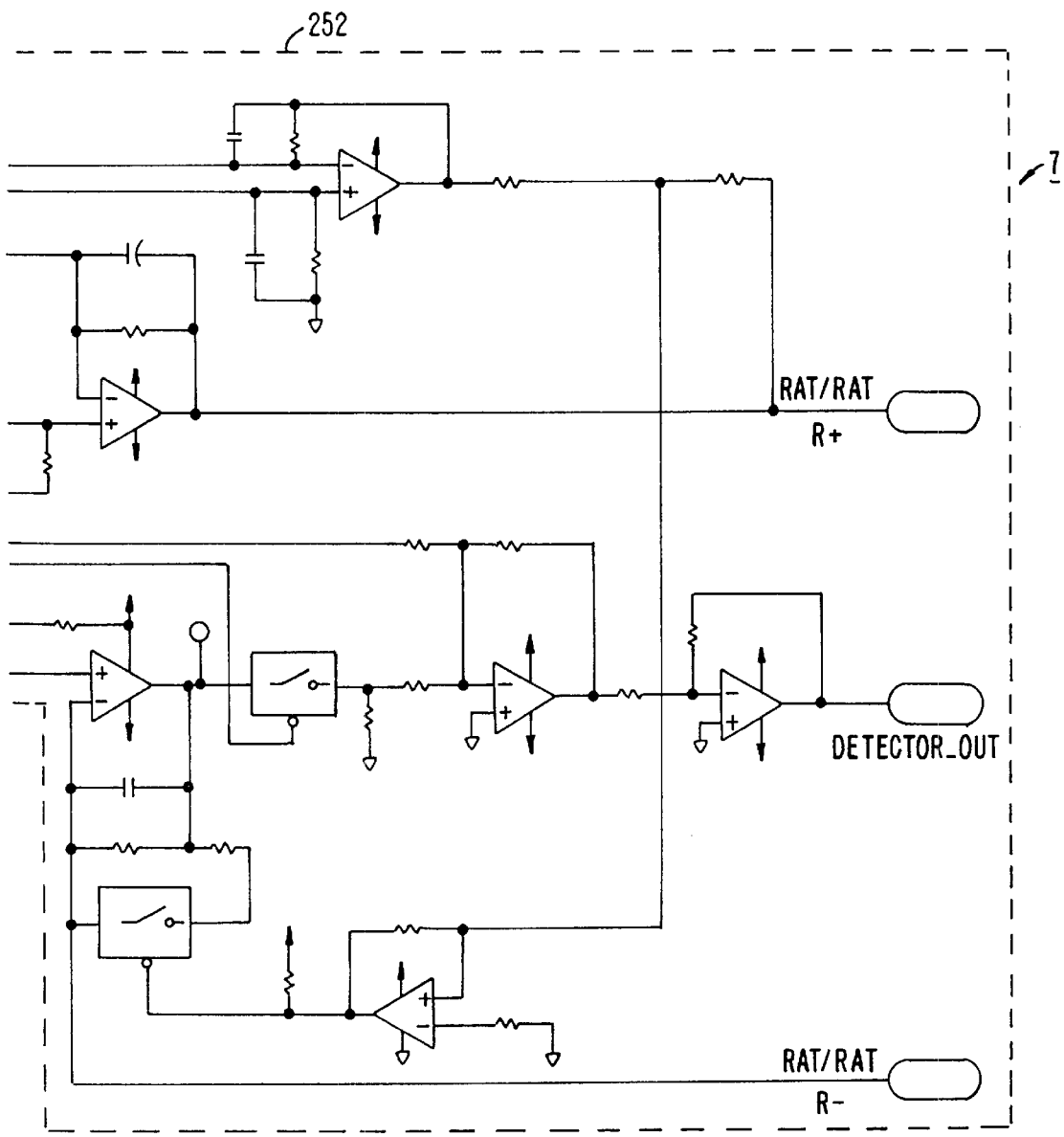
Figures 7, 7A:
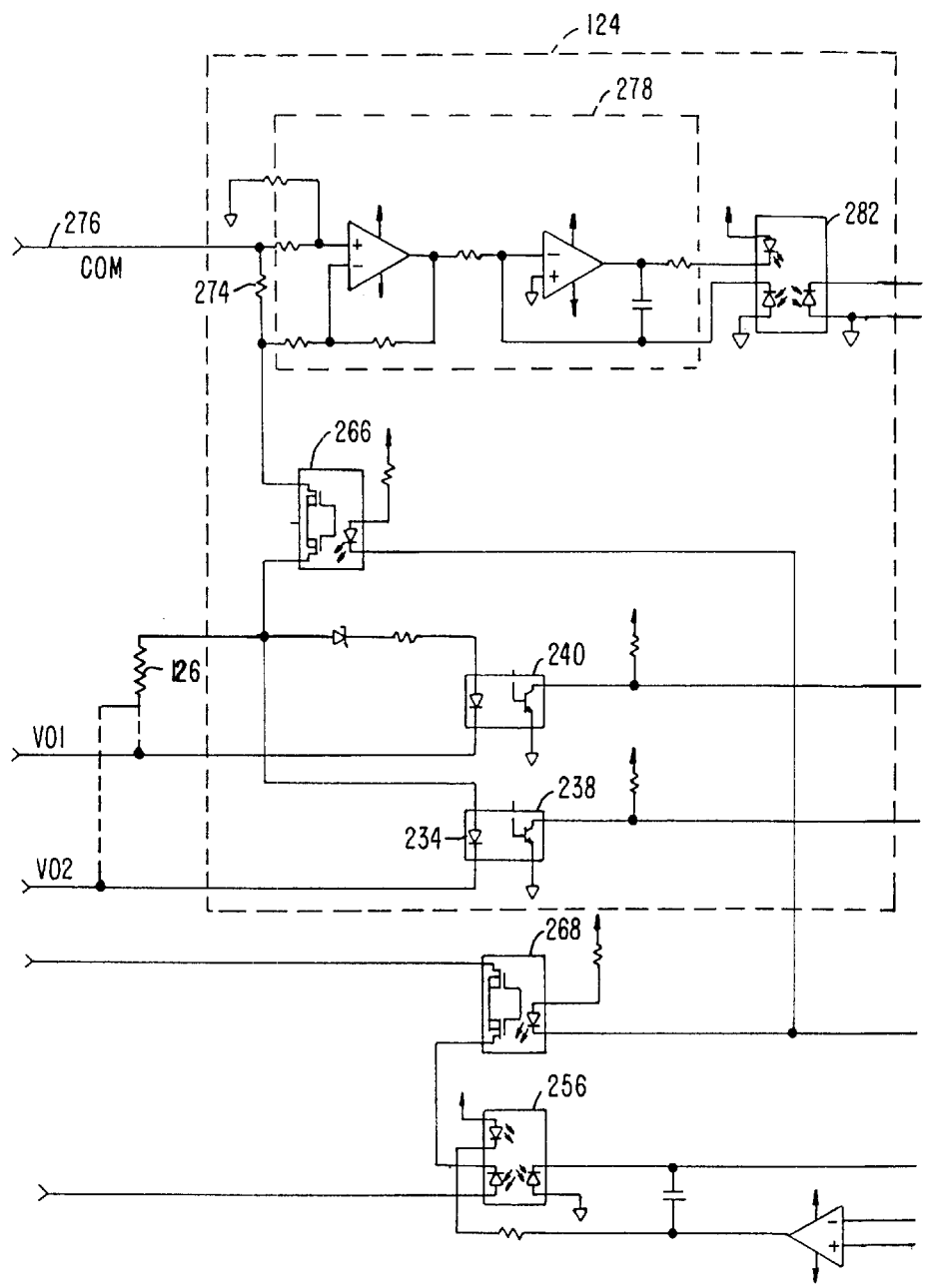
Figure 7B:
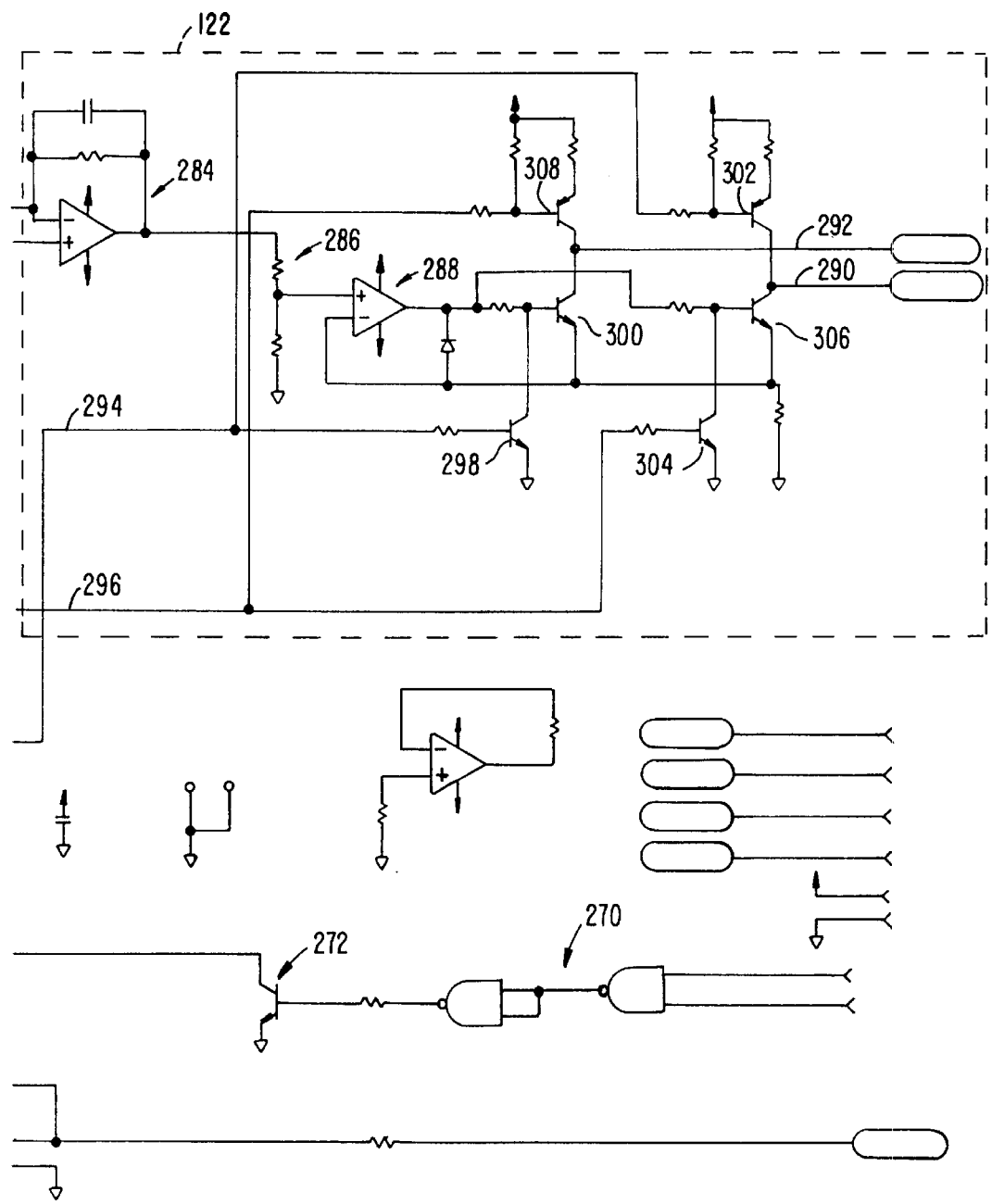
Figures 8, 8A:
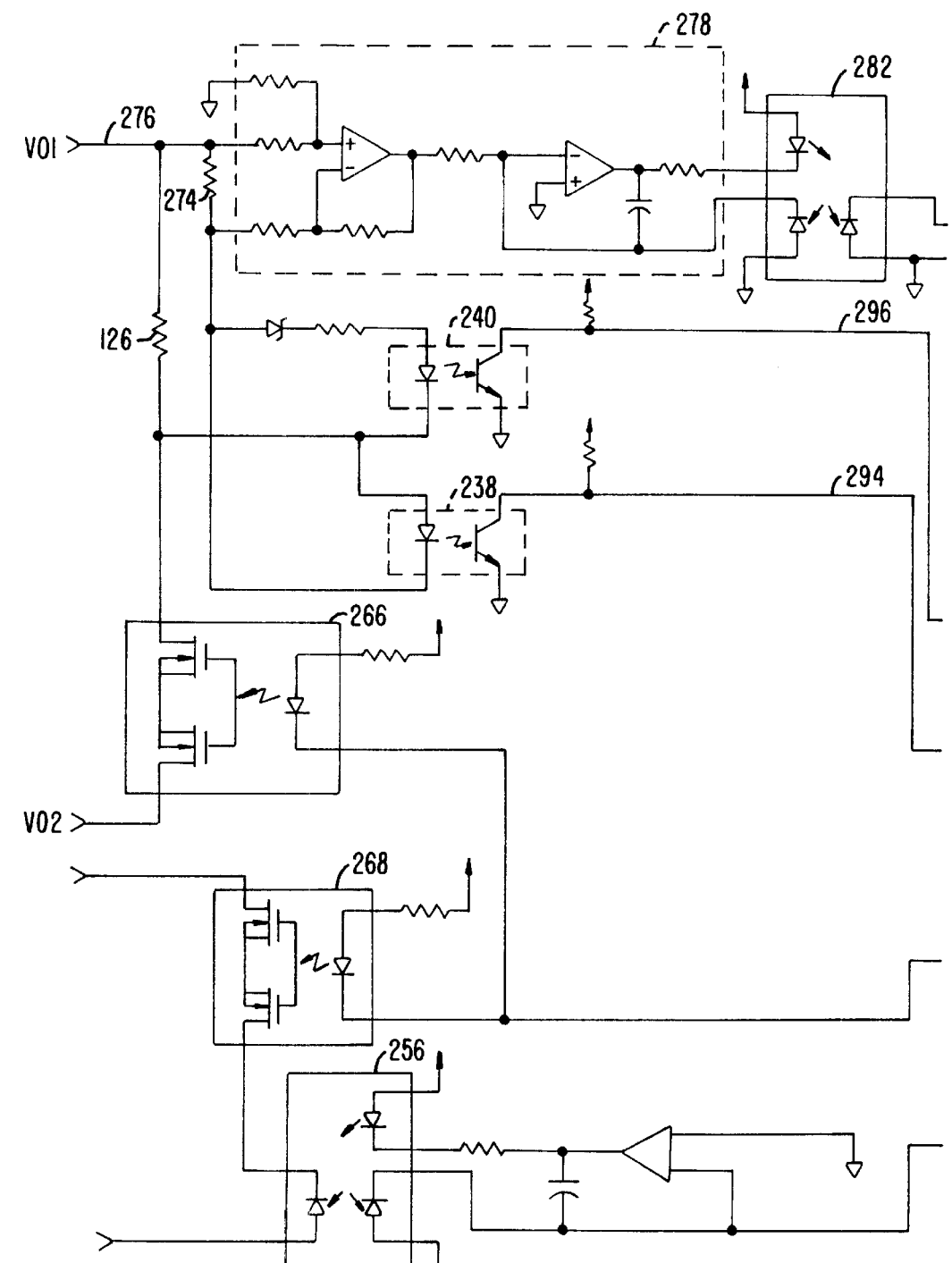
Figure 8B:
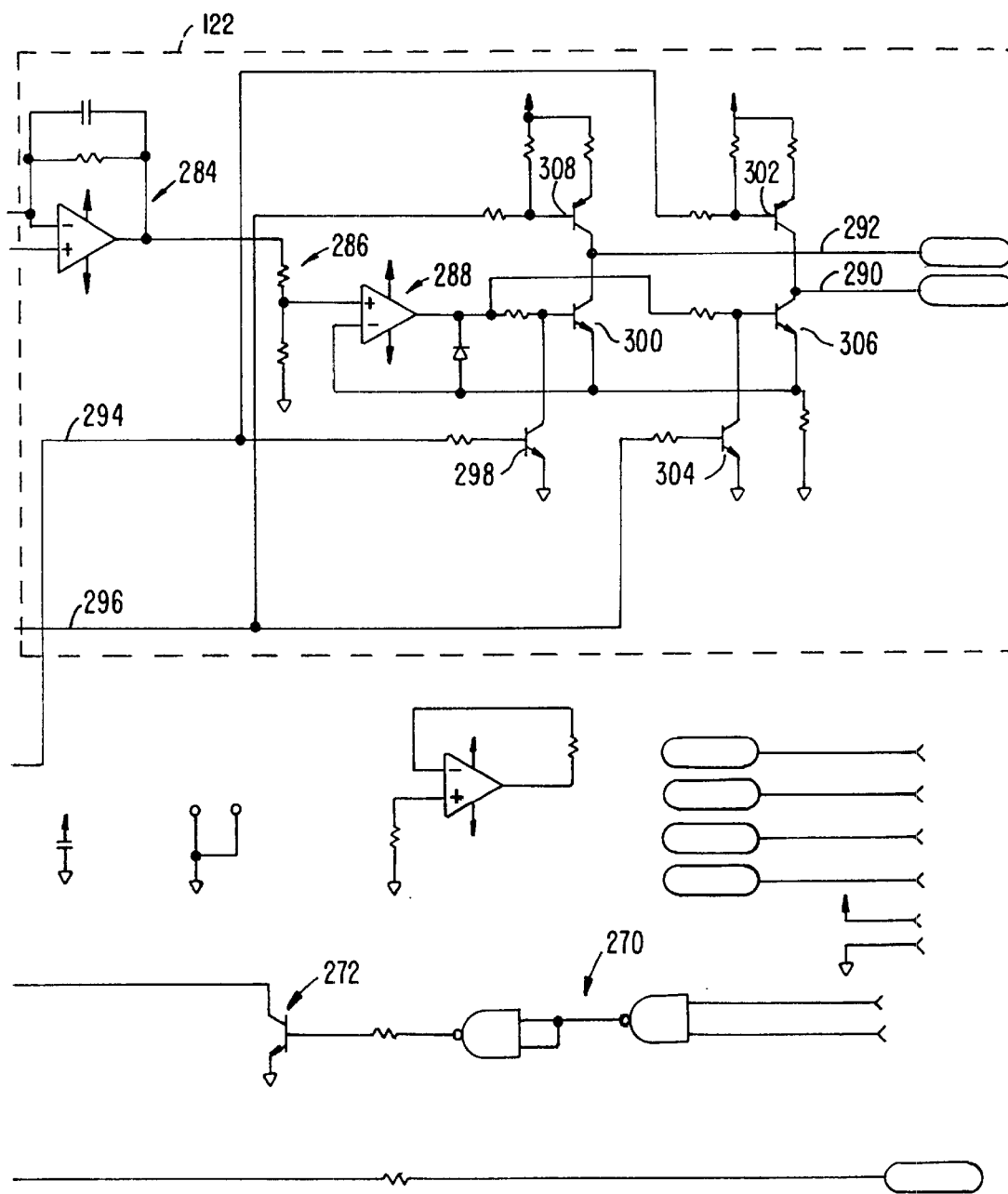
Figure 9B:
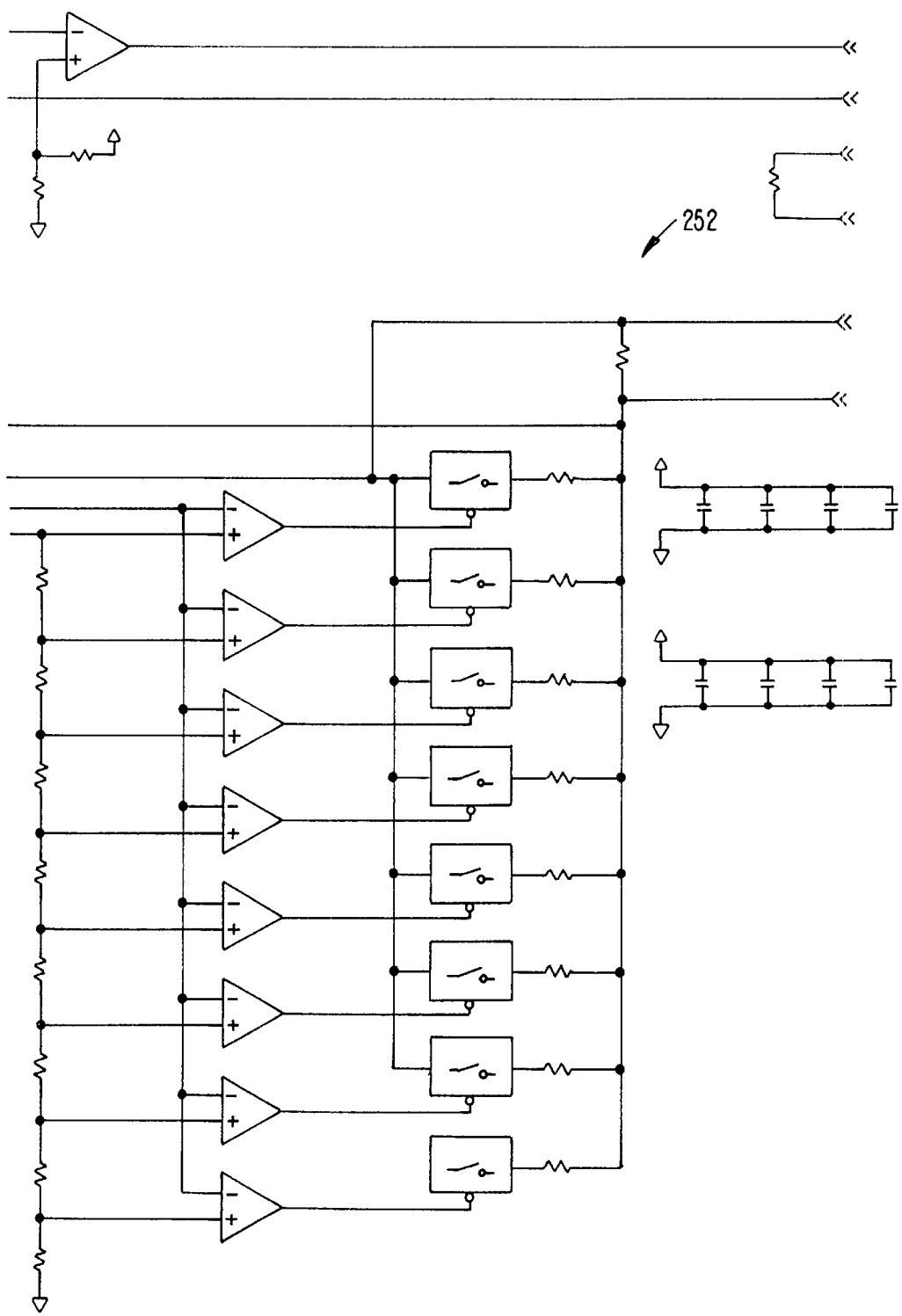

FIGS. 6–9 are circuit diagrams illustrating the embodiments of FIGS. 3 and 4 in more detail. FIGS. 6, 7 and 8 illustrate the components which would be on motherboard 226 of FIG. 2, while FIG. 9 illustrates the components on daughterboard 228. FIG. 6 shows the components of RAT/RAT conversion circuit 252, which continues in the circuitry on the daughterboard, as shown in FIG. 9. FIG. 6 also illustrates the circuitry for power supply 258. FIG. 6 also shows the detector 116 in probe 102, along with the amplifier circuit 250 in adapter 200.

FIGS. 7 and 8 illustrates the circuit details of LED drive circuit 122, and also shows opto-isolators 238, 240 for the LED drives, and opto-isolator 256 for the detector. FIG. 7 illustrates the three-wire embodiment, and FIG. 8 illustrates the two-wire embodiment.

In the three-wire embodiment shown in FIG. 7, resistor 126 is shown between common line 276 and one or the other of LED drive lines VO1 and VO2. As can be seen, the circuitry connected to these lines will not conduct any significant current at a voltage level of approximately 0.5 volts. This allows the value of resistor 126 to be read by applying a 0.5 volt signal between common (COM) line 276 and to whichever of lines VO1 and VO2 resistor 126 is connected.

In the two-wire embodiment shown in FIG. 8, resistor 126 is shown between LED drive lines VO1 and VO2. As can be seen, the circuitry connected to these lines will not conduct any significant current at a voltage level of approximately 0.5 volts. This allows the value of resistor 126 to be read by applying a 0.5 volt signal between lines VO1 and VO2.

In both FIGS. 7 and 8, additional opto-isolators 266 and 268 are provided to disable the circuitry in response to a disconnect signal provided through circuit 270 to a transistor 272, which would activate the opto-isolators. Opto-isolator 266 is in series with resistor 126 and the opto-isolators 240 and 238 for the drive LEDs, while opto-isolator 268 is in series with the detector output opto-isolator 256.

LED drive circuit 122 receives an input from a small resistor 274 in series with node 276. The amplitude of an applied signal is detected through amplifier 278. It is important to detect the amplitude in order to determine the current levels to drive the LEDs with, since the monitor will use a feedback loop to set the intensity to an appropriate level. The amplified signal is provided through an additional optical isolator 282 to LED drive circuit 122. From there, the signal is applied to another amplifier 284, which provides through a voltage divider 286 a voltage level to a current drive circuit 288.

The current from drive circuit 288 is provided either to an IR LED drive line 290, or a RED LED drive line 292. Which one of these is activated is controlled by the signals from opto-isolators 238 and 240 on IR sync line 294 and RED sync line 296, respectively. When opto-isolator 238 pulls line 294 active low, it turns on transistor 302 and turns off transistor 298 (which turns on transistor 300). Since line 296 is inactive high, it turns off transistor 308 and turns on transistor 304 (which turns off transistor 306). Current flows out of line 290 through the IR LED and into line 292. When opto-isolator 240 pulls line 296 active low, it turns on transistor 308 and turns off transistor 304 (which turns on transistor 306). Since line 294 is inactive high, it turns off transistor 302 and turns on transistor 298 (which turns off transistor 300). Current flows out of line 292 through the red LED and into line 290. The current is limited, preferably to a maximum of 50 mA, to limit the temperature at the patient/probe interface, and avoid potential patient burns. This limiting is done by scaling the gain in the current source.

Though the invention has been described with reference to certain preferred embodiments thereof, it is not to be limited thereby. For example, in addition to the opto-isolators, additional series or parallel components may be used to match the forward voltage characteristics of the expected LED more closely. Numerous electronic elements other than the phototransistors and transistors described herein could be utilized to effectuate the electronic switching. For example, a light emitter other than an LED could be used, with its terminals broadly referred to as an emitter drive terminal and an emitter output terminal, rather than an anode and cathode. Alternatively, the adapter could be designed to allow the two-lead portion of the adapter to connect to either a two-lead oximeter or a two-lead probe, rather than being specialized to just one of these orientations. Similarly, the three-lead portion of the adapter could connect to either a three-lead monitor or a three-lead probe.

Alternately, instead of resistor 126, another element may be used to convey information or unlock the oximeter to allow use of a sensor. For example, a semiconductor chip providing digital data may be used to provide more complex coding information than a simple resistor can provide. Certain embodiments of the oximeter may expect such a digital chip to be present. Such a chip could be two-lead memory chip, such as is available from Dallas Semiconductor. All such equivalents are encompassed by the invention, the invention only being limited by the appended claims.

What is claimed is:

1. An oximeter adapter, comprising:

at least first and second oximeter LED drive input lines connectable to oximeter LED drive output lines;

a pair of probe output lines connectable to probe LED drive input lines of an oximeter probe;

a coding element connected across said oximeter LED drive input lines;

an LED drive circuit, connected between said coding element and said pair of probe output lines, for providing a drive signal to said pair of probe output lines in response to signals on said oximeter LED drive input lines.

2. The oximeter adapter of claim 1 wherein said coding element is a resistor.

3. The oximeter adapter of claim 2 wherein said resistor has a value related to a value of an LED in an attached probe.

4. The oximeter adapter of claim 2 wherein said LED drive circuit draws an amount of current, at a predetermined low voltage, which is small enough to allow measurement of a value of said resistor.

5. The oximeter adapter of claim 1 wherein said coding element is a semiconductor chip.

6. The oximeter adapter of claim 1 further comprising a third input line.

7. The oximeter adapter of claim 1 further comprising:

an LED drive sensing circuit coupled between said oximeter LED drive input lines and said LED drive circuit.

8. The oximeter adapter of claim 7 wherein said LED drive sensing circuit includes a pair of optical isolator elements.

9. The oximeter adapter of claim 1 further comprising:

a conversion circuit coupled between a photodetector output from said probe and a photodetector input to an oximeter for modifying a detector signal to account for differences between a wavelength of an LED in said probe and a wavelength expected by said oximeter.

10. An oximeter system comprising:

(a) an oximeter including an LED drive circuit, with a pair of oximeter LED drive output lines: a photodetector sensor circuit, connected to a photodetector input line; and (b) an oximeter adapter, including a pair of oximeter LED drive input lines connectable to said oximeter LED drive output lines;

a pair of probe output lines connectable to LED drive input lines of an oximeter sensor;

a coding element connected across said oximeter LED drive input lines;

an LED drive circuit, connected between said coding element and said pair of probe output lines, for providing a drive signal to said pair of probe output lines in response to signals on said oximeter LED drive input lines.

11. The oximeter system of claim 10 wherein said oximeter adapter further comprises a third input line.

12. The oximeter system of claim 10 wherein said oximeter adapter further comprises:
   an LED drive sensing circuit coupled between said oximeter LED drive input lines and said LED drive circuit.

13. The oximeter system of claim 12 wherein said LED drive sensing circuit includes a pair of optical isolator elements.

14. The oximeter system of claim 10 wherein said oximeter adapter further comprises:
   a conversion circuit coupled between a photodetector output from said probe and a photodetector input to said oximeter for modifying a detector signal to account for differences between a wavelength of an LED in said probe and a wavelength expected by said oximeter.

* * * * *